United States Patent [19]
Ishikawa et al.

[11] Patent Number: 5,984,854
[45] Date of Patent: Nov. 16, 1999

[54] METHOD FOR TREATING URINARY INCONTINENCE AND AN APPARATUS THEREFOR

[75] Inventors: Norio Ishikawa, Kawasaki; Shin Suda, Tokyo; Hidehiro Hosaka, Sayama, all of Japan

[73] Assignee: Nihon Kohden Corporation, Tokyo, Japan

[21] Appl. No.: 08/800,709

[22] Filed: Feb. 14, 1997

[30] Foreign Application Priority Data

Feb. 15, 1996 [JP] Japan .................................. 8-052373

[51] Int. Cl.⁶ ...................................................... A61N 2/02
[52] U.S. Cl. ...................................................................... 600/9
[58] Field of Search ................................ 600/9–15, 407, 600/410, 411, 415, 421, 422

[56] References Cited

U.S. PATENT DOCUMENTS

| | | | |
|---|---|---|---|
| 4,428,366 | 1/1984 | Findl et al. .......................... | 600/14 |
| 4,875,485 | 10/1989 | Matsutani .............................. | 600/415 |
| 5,061,234 | 10/1991 | Chaney . | |
| 5,344,384 | 9/1994 | Ostrow et al. ....................... | 600/13 |
| 5,453,073 | 9/1995 | Markoll .................................. | 600/14 |

FOREIGN PATENT DOCUMENTS

| | | | |
|---|---|---|---|
| 39 37 793 A1 | 5/1991 | Germany . | |
| 93 00 499 | 5/1993 | Germany . | |
| 91/15263 | 10/1991 | WIPO ................................. | 600/13 |
| WO 94/13357 | 6/1994 | WIPO . | |
| WO 95/21655 | 8/1995 | WIPO . | |
| WO 95/27533 | 10/1995 | WIPO . | |

*Primary Examiner*—Samuel Gilbert
*Attorney, Agent, or Firm*—Hoffmann & Baron, LLP

[57] ABSTRACT

A method for treating urinary incontinence which consists of delivering a train of current pulses through one or more magnetic stimulation coils to induce a train of magnetic flux pulses, which then induce an eddy current within the body, thereby to stimulate a group of pelvic floor muscles, the pudendal nerve, the external urethral sphincter, or the tibial nerve.

28 Claims, 8 Drawing Sheets

METHOD FOR TREATING URINARY INCONTINENCE AND AN APPARATUS THEREFOR

BACKGROUND OF THE INVENTION

1. Field of the Invention

This invention relates to a method for treating urinary incontinence and an apparatus therefor in such a manner as to induce an eddy current in the physiological body by means of a magnetic stimulation coil which produce a magnetic pulsive flux under the suppliment of current pulses.

2. Description of the Related Art

Urinary incontinence or leakage of urine contrary to the patient's will has been neglected because it is not a disorder threatening the life of the patient. This urological malfunction, however, interferes often with everyday activities of the patient, and thus appropriate treating measures for it have been desired.

Such desire is especially manifest nowadays when aged population have been increasing rapidly, and patients with this bladder malfunction tend to grow in association. This malfunction is seen among children as well as among elderly people whether they are men or women, and patients with spinal cord injuries often resulting from traffic accidents are also frequently afflicted with this malfunction. Such tendencies spur the urge toward a good remedy for this involuntary leakage of urine because such remedy would be greatly helpful for the improvement of quality of life of the patient.

Conventional methods for treating urinary incontinence include, besides those dependent on the use of medication or surgery, the electric stimulation which consists of applying stimulating electrodes to the patient, and delivering electric pulses therefrom to contract relevant muscles, thus preventing the occurrence of stress or urge incontinence. Those electric treatment methods have been widely known. The main elements to be stimulated in those methods include the lumbosacral plexus innervating the lower urethra, and a group of muscles forming the pelvic floor (pelvic floor muscle group) and the external urethral sphincter. The stimulating electrodes are usually inserted into anus or vagina, so that they can gain close access to those nerves and muscles from the body surface. To be inserted into vagina, the stimulating electrodes, which are to be connected to a pulse generator, take a plug form 2 cm in diameter and 4 cm in length, while they take a tympanic form of similar size to be inserted into anus. After the electrodes having been attached to the body, repetitive current pulses of a frequency of several to several tens Hz, a peak current of 1–100 mA and a width of 50 $\mu$s–5 ms are passed through the body from the body surface.

Generally, pulses with a frequency of several Hz are indicated for urge incontinence while pulses with a frequency of several tens Hz for stress incontinence. The treatment consists usually of delivering electric pulses for 15 minutes once daily and repeating the session for two to four weeks.

During this treatment, the pelvic floor muscle group is stimulated by pulses delivered from the body surface, and put into action. Therefore, dystrophied muscles become activated, and come to have a strength necessary for constricting the passage of urine. This is the reason why this method is effective for the treatment of stress incontinence. To cope with urge incontinence which results from involuntary contraction of the bladder, what is necessary is to stimulate the pudendal nerve arising from 2nd to 4th sacral nerves or its branches, because the impulse from that nerve can inhibit reflexly the involuntary contraction of the bladder, thereby preventing involuntary leaks of urine.

An alternative method, which is also widely known, consists of placing surface electrodes on the external pudendal region or its vicinity to stimulate the pudendal nerve. When sessions comprising repetitive stimulations are repeated over a period, the effect persists even after cessation of the treatment.

It is also known that these treatments are effective for the treatment of bladder pain, frequent urination and bed-wetting as well.

With these methods dependent on the use of plug-type electrodes, however, the patient must insert the electrodes into anus or vagina each time he/she receives the treatment.

This is very disagreeable and humiliating for the patient.

Particularly if children, unmarried women or elderly persons have to be treated with these methods, and they are forced to do such actions for the treatment, they will never fail to feel a strong aversion to such requirements which may, in extreme cases, lead to complete denial of the treatment or treatment continuation. If a strong stimulating current is used to strengthen its effect so that the period necessary for the treatment may be shortened, it may cause pains or, in worst cases, burns.

In view of this, stimulus intensity is gradually raised in a pilot study, and the intensity of treatment stimulation is set to a level which does not cause any discomfort in the patient, or to a tolerable limit. However, the effect of a stimulus varies widely according to the configuration of the electrodes through which it is delivered, and to the sensitivity of the patient. Further, if the patient has a disordered sensitivity, the intensity of stimulus may happen to be so large as to cause him/her burns. Thus, these methods pose many problems which have remained to be solved. These methods further require frequent insertion,/removal of the electrodes into/from vagina or anus, which is necessarily associated with the danger of infection and inflammation. Accordingly, these methods, allegedly non-invasive, are close to an invasive treatment.

To alleviate the above problems, a number of methods have been developed wherein surface electrodes are pasted onto the skin around the pudendal region. However, the same problems still persist: pains and burns are more liable to occur with the progressive increase of stimulation, and daily application/removal of surface electrodes may lead to irritation/inflammation of the involved skin. This method is not acceptable to the patient whose sensitivity is impaired.

SUMMARY OF THE INVENTION

In view of the foregoing, the object of this invention is to offer a method for treating urinary incontinence and an apparatus therefor, which is non-invasive, arouses no discomfort, pains, nor humiliation, and can be applied to any persons regardless of age and sex.

This invention starts from having paid attention to the fact that supply of a magnetic pulse field, instead of passage of a current pulse through the physiological body, can induce an eddy current, and is based on the development of a magnetic stimulation method by which magnetic flux pulses penetrating into the body to thereby reach the pelvic floor muscle group, the external urethral group, or the lumbosacral nerve plexus, of which stimulation is effective for the treatment of urinary incontinence are produced by an external body portion.

Japanese Unexamined Patent Publication No. 57-22770 discloses a magnetic treatment apparatus wherein a capacitor which has been charged by a DC source discharges through a coil, and that the discharging current is interrupted with a switch which is turned on and off at a predetermined frequency, thereby generating magnetic fluxes around the coil for stimulation.

According to this magnetic treatment apparatus a power circuit with a small internal resistance can generate magnetic flux pulses of a frequency other than that of commercial power line, and switching of pulse modes can also be achieved quickly.

According to this method, however, the stimulating magnetic coils are attached to the body through suction discs to stimulate local blood flow, thereby moderating pains associated with muscle exertion or rheumatoid arthritis. The same publication does not give any mention about the treatment of urinary incontinence.

To achieve the above-described object, the method of this invention for treating urinary incontinence consists of applying a magnetic stimulation coil at a body portion within the range from the waist to the lower limbs, and supplying a train of current pulses to the coil to generate a train of magnetic flux pulses. The magnetic flux invades the body, and the resulting eddy current readily stimulates the pelvic floor muscle group, the pudendal nerve arising from 2nd to 4th sacral nerves which is scarcely accessible by the current stimulation applied from the body surface, the external urethral muscle, or the tibial nerve. The apparatus of this invention for treating urinary incontinence comprises a coil install tool installed in a room and provided with one or more magnetic stimulation coils which are set to a body portion of the patient within the range from the waist to lower limbs, and coil feed means for feeding the magnetic stimulation coils so as to produce a train of magnetic flux pulses therefrom. Another apparatus comprises one or more body attached wears which are provided with one or more magnetic stimulation coils for producing a magnetic flux at or around the pudendal region of the patient, coil feed means for feeding the magnetic stimulation coils so as to produce a train of magnetic flux pulses therefrom, and a battery for feeding the coil feed mean.

With the conventional electric stimulation dependent on the use of plug-form electrodes or surface electrodes, a large amount of current applied flows through the superficial skin in direct contact with the electrodes, which ends as a sheer loss, and only a small fraction of the current flows through effective region. Thus the stimulation efficiency becomes very low. By contrast, the method of this invention is free from loss associated with superficial flow of a stimulating current, and readily induces an eddy current at deep regions effective for treatment. The method of this invention further allows magnetic fluxes to extend wider, and to penetrate deeper so that a smaller current effectively stimulate. Accordingly, increasing current intensity does not always lead to evocation of pain sensation.

With the method of this invention, the patient can treat his/her urinary incontinence by only setting a magnetic stimulation coil to his/her body portion through the garments so that an eddy current is induced in the lumbosacral nerve plexus, the pelvic floor muscle group, the external urethral muscle, or the tibial nerve. The superficical shape for producing magnetic fluxes can be adjusted so as to comply with any individual symptoms and requirements. When a large current is chosen, its effective area widens, and thus placement of the coil is not restricted so that the coil is easily set to the patient. The coil is placed in a coil install tool at home or in a hospital, and thus the patient is applied with strong magnetic field for the treatment of urinary incontinence while keeping a natural posture.

Because the treatment does not cause any noticeable pain, the patient can readily accept continuation of the treatment, which leads further to the enhancement of the treatment effect.

This method can be applied to any persons, young or old, or male or female. In addition, the method of this invention can be applied for the treatment of disturbed micturition and back pain as well as urinary incontinence, because it allows stimulation of the urinary bladder, and nerves and muscles innervating the urinary bladder.

The portable type of the inventive apparutus allows to stimulate not only the pudendal nerve but also the lumbosacral nerve plexus including the sciatic and tibial nerves, which is effective for the control of urge incontinence. It allows a longer stimulation with a weak magnetic field than does the stationary type while being engaged in everyday activity, which further contributes to the enhancement of its therapeutic effect.

BRIEF DESCRIPTION OF THE DRAWINGS

FIG. 2 is a plan of the inner construction of coil assembly wherein FIG. 2A shows that of the same apparatus and FIG. 2B shows that of another embodiment.

FIG. 5 illustrates a stationary type of the apparatus using a bed wherein 5A is its side view, FIG. 5B its plane view, and FIG. 5C a modification of this type.

FIG. 7 illustrates a stationary type of the apparatus using a stand which allows the patient to be treated while standing wherein FIG. 7A is its side view, FIG. 7B its plane view, FIG. 7C a modification of the magnetic stimulation coil and FIG. 7D another modification thereof.

FIG. 8 illustrates a stationary type of the apparatus using a stand which allows the patient to be treated while standing wherein the coil is mounted on the arm of a stand and the patient can receive treatment while standing, wherein FIG. 8A is its side view and FIG. 8B its flat view.

DETAILED DESCRIPTION OF THE PREFERRED EMBODIMENTS

Figure 1:
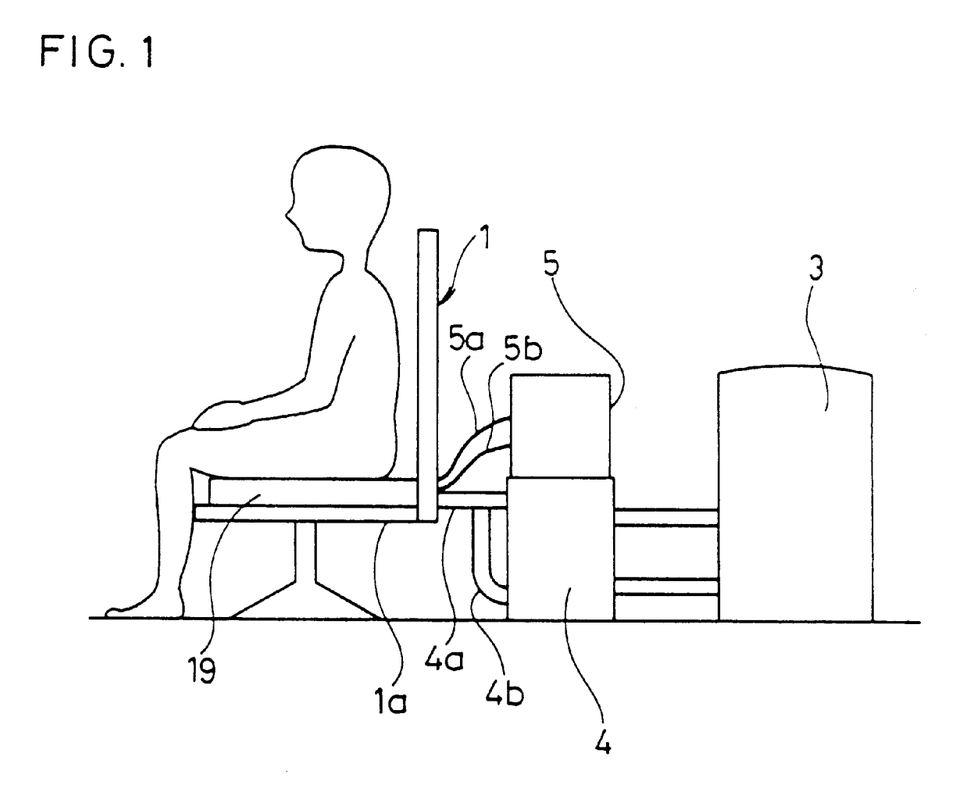
FIG. 1 is a side view of a stationary type of the apparatus using a stool in accordance with the inventive embodiment.
Figure 2A:
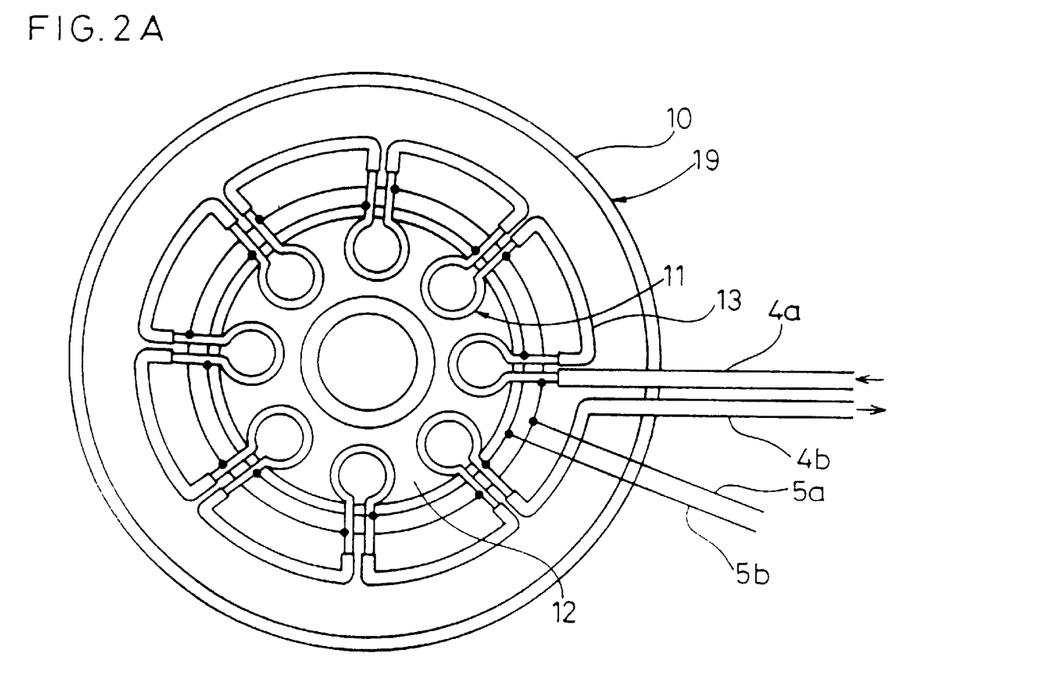
Figure 3:
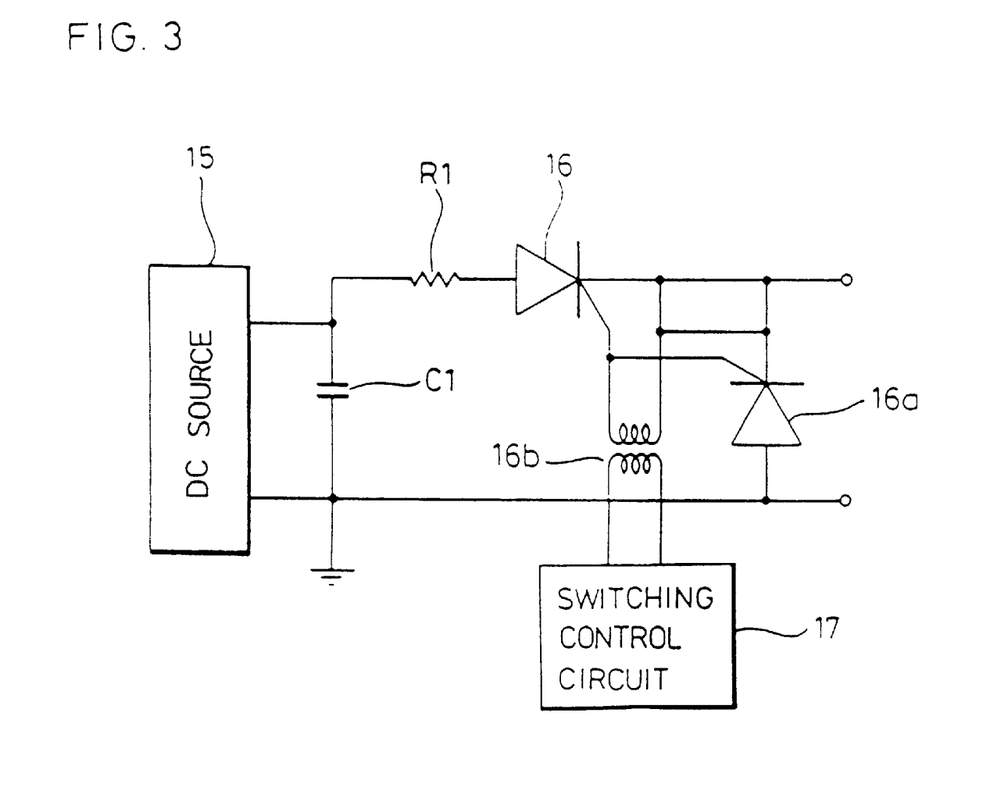
FIG. 3 is a circuit diagram of coil feed means of the same apparatus.

FIGS. 1 to 3 illustrate a stationary coil install tool, used for the treatment of urinary incontinence. A coil assembly 19 illustrated in FIG. 2A is placed on the seat 1a of the stool.

A disc-form housing 10 made of a synthetic resin contains at its center the coil assembly which consists of a group of hold coils 12 each of which is made of a hollow conductor wound one turn into a magnetic stimulation coil 11 and then tightly covered with a synthetic resin. Each magnetic stimulation coil 11 is connected at both ends to an insulated water feed pipe 13, one end there of being conected to a water feed pipe 4a from a water cooling apparatus 4, and the other end to a water discharge pipe 4b so that cold water from the water cooling apparatus can circulate through the group of coils. Individual magnetic stimulation coils are connected in parallel together and through lead wires 5a and 5b to the output terminals of a feed apparatus 5 which contains a coil feed means to supply current to the magnetic stimulation coils.

FIG. 3 shows a circuit diagram of the coil feed means.

It has a DC source 15 which provides a voltage between 100V and 3 kV, a capacitor C1 with a capacity of about 300 $\mu$F which is charged with the voltage supplied by the DC source, a thyristor 16 which supplies the charge voltage to the magnetic stimulation coils through a protective resistor R1, another thyristor 16a which absorbs a reversed voltage developed during switch-off, and a switching control circuit 17 which controls switching of those thyristors based on a charge-discharge sequence. The switching control circuit can adjust the repetitive frequency of stimulation in the range of 1 Hz to 100 Hz. The apparatus is so constructed as to give a peak magnetic flux of 0.01 tesla when a current pulse with a width of 100 $\mu$s is passed through the group of magnetic stimulation coils, and 3 tesla when a maximum current pulse of about 3000 A is used, provided that the structure of the magnetic stimulation coils 11, the voltage of the DC source 15 and the capacitance of the capacitor C1 are properly adjusted and chosen.

When the patient sits on the seat 1a which contains the coil assembly 19, the apparatus is put into operation and a magnetic flux develops from the anal region upwards. At the same time the magnetic stimulation coils becomes a heater of 1–70 W because of loss of current resulting from the resistive component of the coils. When the heating output of the magnetic stimulation coils exceeds 5 W or so, cooling water is circulated through the magnetic stimulation coils, thereby preventing the occurrence of low temperature burns as well as high temperature burns associated with high outputs. This maneuver allows a continuous treatment lasting as long as 15 minutes. With conventional methods, main stimulated regions include superficial muscles, the inferior rectal nerve innervating the skin around anus and the external anal sphincter, the perineal nerve innervating the perineal skin and muscles, the dorsal nerve of penis and the dorsal nerve of clitoris. On the other hand the apparatus in accordance with this invention a magnetic flux invades deeply into the body to induce an eddy current and therefore not only the muscle group forming the pelvic floor but also branches from 2nd to 4th sacral nerves including the pudendal nerve, and the external urethral sphincter itself are effectively stimulated.

For the treatment of urge incontinence, the frequency is set to several Hz while for the treatment of stress incontinence it is set to several tens Hz. The patient can use the apparatus by just sitting on the stool 1 without removing his/her garments.

The switching control circuit 17 can be so modified as to produce, besides a train of single pulses, a train of double pulses (the upper row of FIG. 4) or successive pulses (the lower row of FIG. 4), each magnetic stimulation pulse having a pulse width of about 100 $\mu$s, thereby to reduce pains associated with stimulation of widened single pulses. Further, DC source having the outputs with the double polarities can be used, although it makes the circuit a little bit more complicated, which allows generation of a train of bipolar pulses (the middle row of FIG. 4), resulting in the large variation of magnetic flux and causing the eddy current to increase without increasing the voltage of the power source. In addition, such apparatus allows generation of pulses in different combinations; trains of single monopolar pulses, a train of bipolar double pulses, etc., and the operator can choose appropriate ones from among them according to the condition of stimulation region or patient's symptoms. With this apparatus, the pulse width is not confined to 100 $\mu$s, can be varied as in conventional apparatuss, and usually set to 50 $\mu$s to 5 ms.

Figure 4:
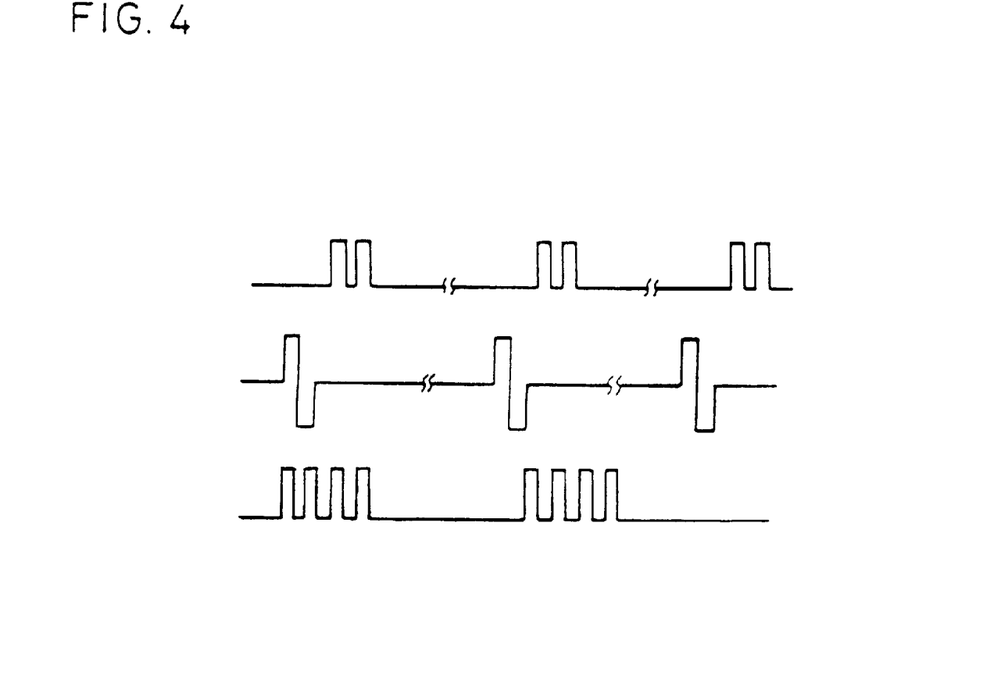
FIG. 4 illustrates the stimulation pulse mode of the coil feed means.

The operator can vary the pulse width at will by installing a plurality of capacitors connected in parallel, and by adjusting the capacity through the choice of appropriate capacitors among them. Electrophysiologically, there exist a relationship called chronaxie which defines the intensity of a current pulse and its width: when one is chosen high, the other can be low to obtain an effective stimulation. Accordingly, when the pulse width of the magnetic stimulation pulse is chosen to be narrow, the charge voltage is chosen to be large while the charge voltage is chosen to be low when the pulse width is chosen to be wide. Therefore, by adjusting properly the intensity and width of a current pulse, the operator can obtain a stimulation that requires the least energy consumption but is still effective.

Figure 2B:
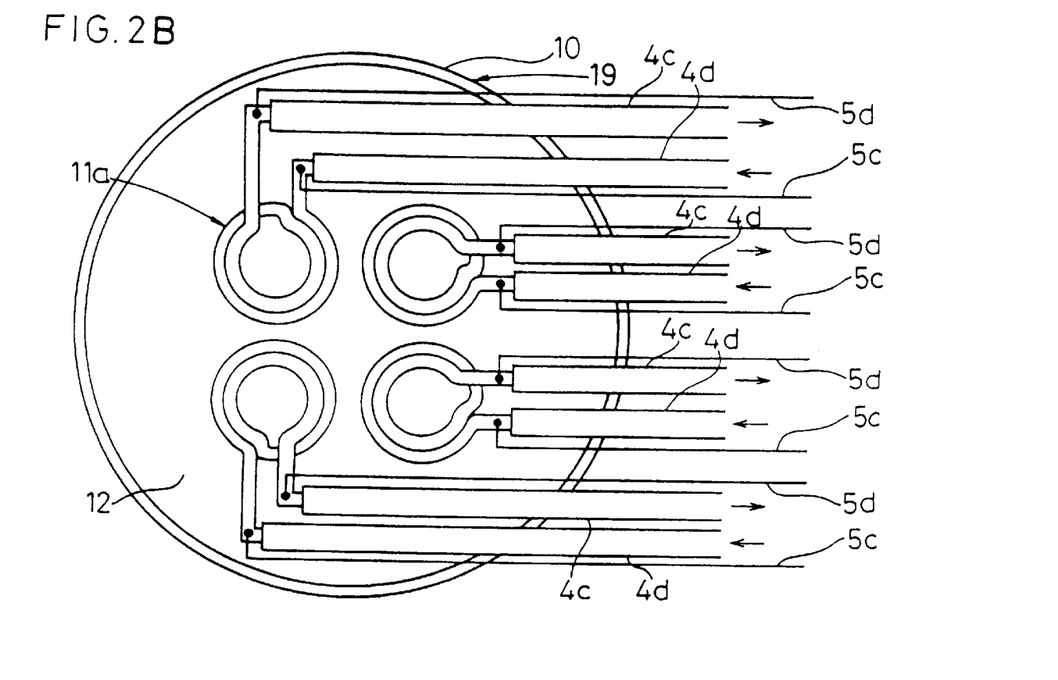

FIG. 2B illustrates the constitution of a second type of the coil assembly 19. Magnetic stimulation coils 11a each consist of a winding having two turns of insulated wires are independently connected to a water feed pipe 4c and a water discharge pipe 4d, and are supplied with current through wires 5c and 5d. With this arrangement it is possible to change the polarity of the magnetic fields developed at the magnetic stimulation coils 11a independently from each other, and thus to change the distribution of magnetic flux density or to strengthen the intensity of magnetic flux passing through the region to be stimulated.

Figure 5A:
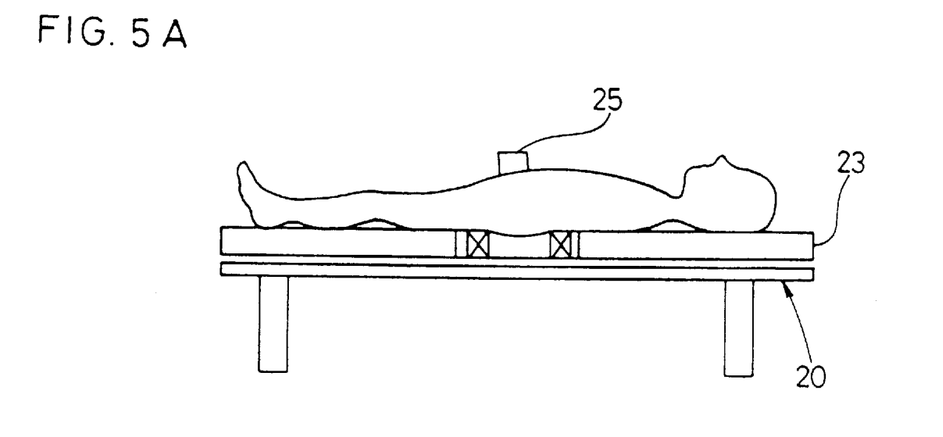

FIG. 5A shows a coil installed tool using a bed 20.

Figure 5B:
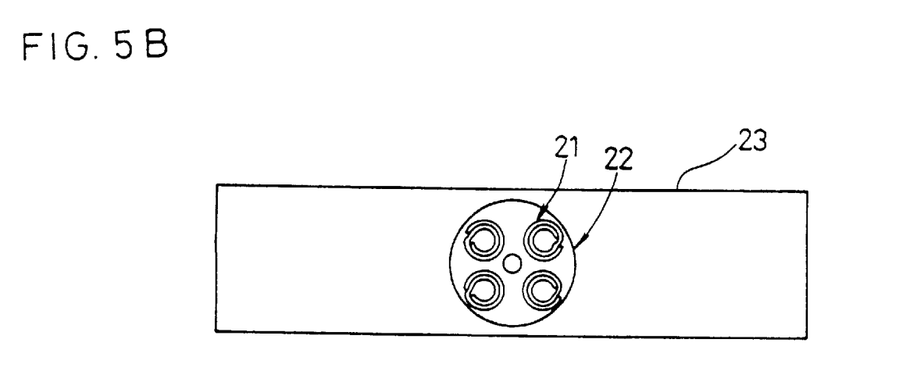

As shown in FIG. 5B, a group of mold coils 22 made of synthetic resin having magnetic stimulation coils 21 embedded in an annular shape is mounted to the region confronting the pelvis in a mat 23. Because with this arrangement a magnetic flux develops from the lower pelvis upwards, it can readily stimulate the perineal nerve, the pudendal nerve including the dorsal nerve of penis or dorsal nerve of clitoris, a group of pelvic floor muscles, and the external urethral sphincter. This method further allows the patient to receive stimulation while lying on the bed, and thus the treatment lasting as long as, say, 15 minutes will be possible. In addition, if a magnetic material 25 such as ferrite is placed on the abdomen, it will help to concentrate stray and diffusive magnetic fluxes onto effective regions.

This maneuver, therefore, allows to exert its effect more efficiently for a same applied voltage. This maneuver is effective for the treatment of both urge and stress incontinence.

Figure 5C:
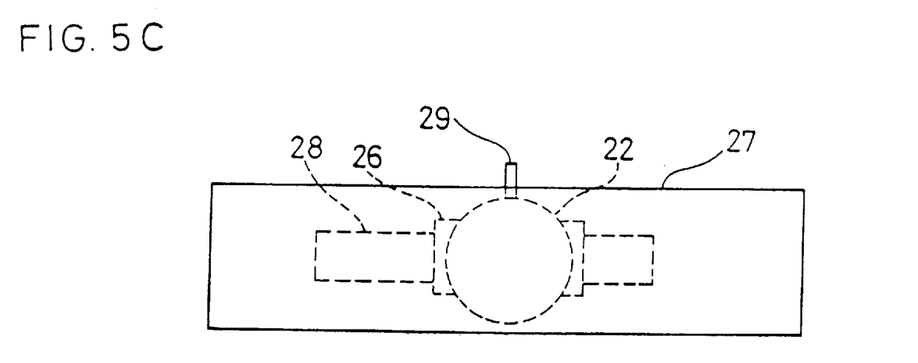

FIG. 5C shows a modification of the coil installed tool using a bed. Instead of a mat 23, a case 27 made of clear synthetic resin is placed on the bed. It contains in its interior a group of mold coils 22, a slider 26 from which a handle 29 sticks out to be operated from outside, and a rail 28 which extends from the position corresponding to the patient's waist to the one corresponding to his knees, and enables the patient's body to move by that distance. This rail can be extended up to the position corresponding to the patient's toes.

Figure 6:
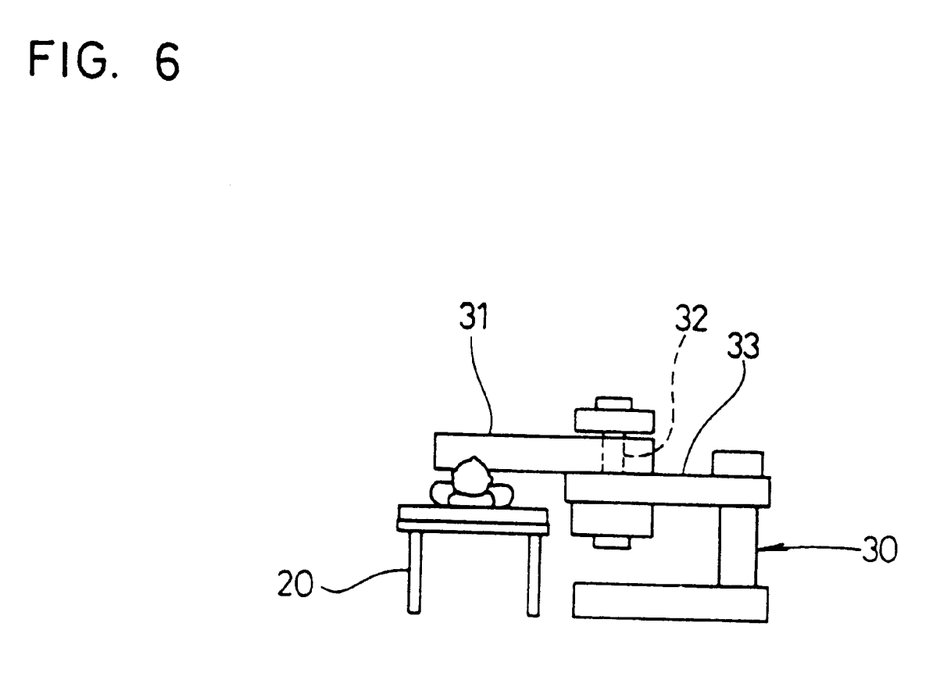
FIG. 6 illustrates a stationary type of the apparatus using a stand close to the patient's bed.

FIG. 6 shows a coil installed tool using a stand. This coil installed tool consists of a stand 30 placed close to a bed 20 and a coil supporting arm 31 containing magnetic stimulation coils. The coil supporting arm 31 is supported rotatably to the supportive shaft 32 of a swing arm 33 so that it can swing by 90° between a position above the bed and the remote position.

When the patient lies on the bed to be ready for stimulation, the coil supporting arm 31 is swung from the remote position to a position above the patient's abdomen. After the arm 31 has been lowered to an appropriate position, a train of current pulses are delivered from a coil feed means constructed in the same manner as above. A further fine positioning of the arm 31 is possible with the adjustment of the swing arm 33 if necessary.

Acording to this apparatus, a magnetic flux develops from the abdomen or its underlying parts, and is effective for the treatment of both urge and stress incontinence.

Figure 7A:
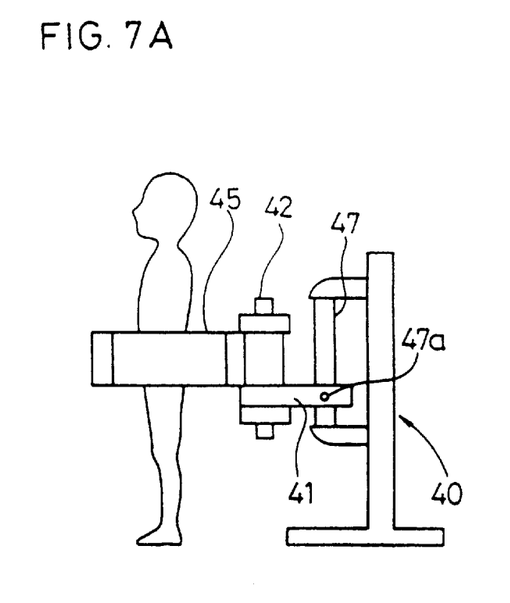
Figure 7B:
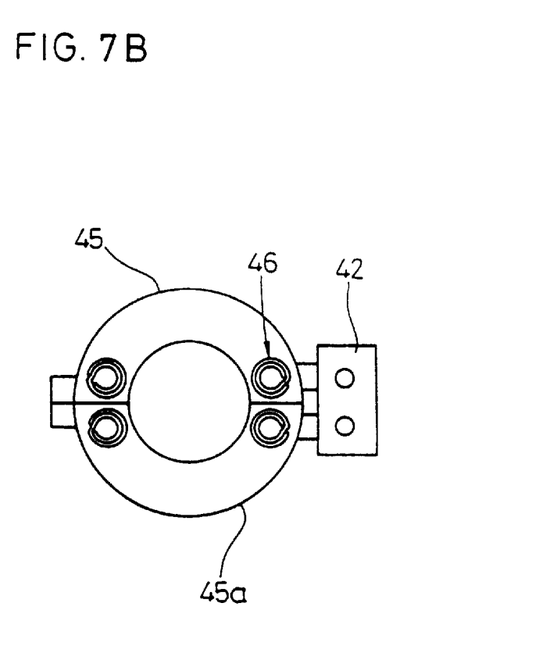
Figure 7C:
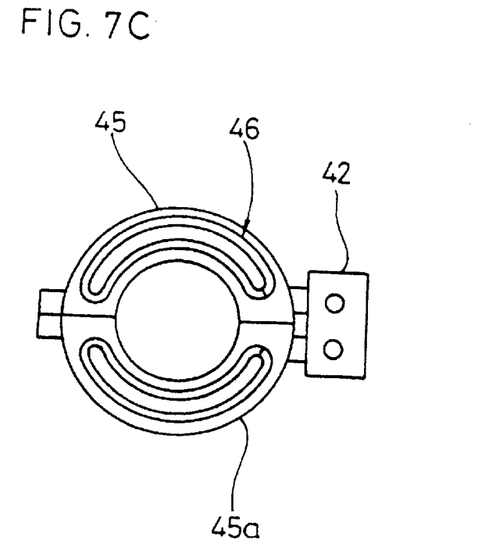

FIG. 7A shows a coil installed tool by which the patient is treated in the standing condition. The coil installed tool comprises a stand 40, a pair of semicircular coil supporting arms 45 and 45a (FIG. 7B) forming a ring for embracing the patient when closed, and a supporting arm 41 which supports the supportive shaft 42 at its distal end and guided by a guide rod 47 to thereby slide up and down with the slide position being locked with a lock screw 47a. The semicircular coil supporting arms 45, 45a contain respectively the magnetic stimulation coils 46 disposed in a circular form and are hinged at the respective proximal ends to the supportive shaft 42. The magnetic stimulation coils 46 may be wound in a semicircular form respectively in arms 45, 45a, as shown in FIG. 7C.

When the apparatus is used for the treatment of the patient with urge incontinence or stress incontinence, the coil supporting arms 45 and 45a are opened, the patient is allowed to enter into the space between the arms, keeping a standing posture, and the arms are closed. Thus, the magnetic stimulation coils 46 are set around the patient's abdomen thereby producing magnetic fluxes from surrounds toward the center. By selecting appropriate combinations of a plurality of magnetic coils, the operator can stimulate any desired regions in the abdomen, or can stimulate with such an intensity as to offer a minimum effective stimulation to the patient, realizing a highly efficient stimulation in terms of power consumption.

Figure 7D:
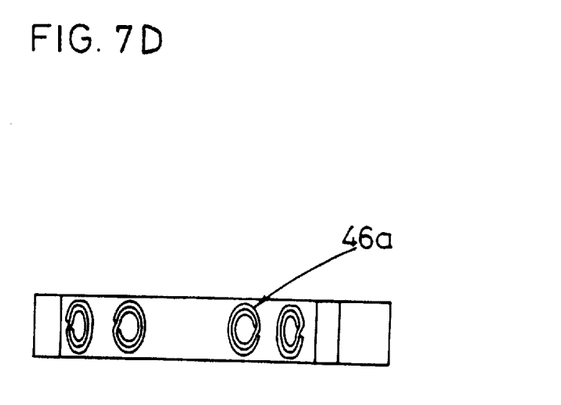

The coil supporting arms 45 and 45a can have magnetic stimulation coils 46a wound in the vertical direction as shown in FIG. 7D. When the magnetic stimulation coils 46 adjacent to each other are supplied with currents having the opposite directions to each other, a magnetic flux dispersing to the perihery is attracted toward the adjacent coil, thereby to be add to each other, then concentrating the induced eddy currents between the adjacent coils 46. This method allows effective stimulation with a very low voltage or a very low power consumption especially when the region to be stimulated exists in the superficial body. Further, by selecting an appropriate pair of adjacent coils, the operator can stimulate desired regions effectively.

Still further, when the coils sandwiching the patient's abdomen on the both sides in the coil supporting arms 45 and 45a are fed in the opposite direction to each other so that the produced magnetic fluxes are attracted by the counterpart allowing an effective stimulation to a deeper region of the physiological body with a lower voltage or a lower power consumption. Magnetic stimulation coil 46a can be so composed as to be replaced with a magnetic material having a high permeability.

Figure 8A:
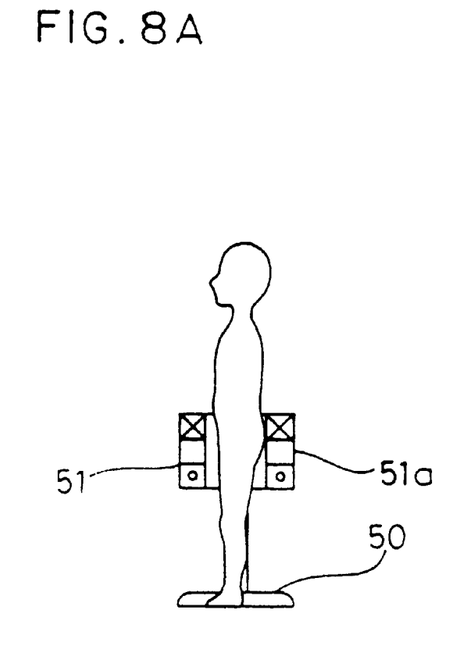
Figure 8B:
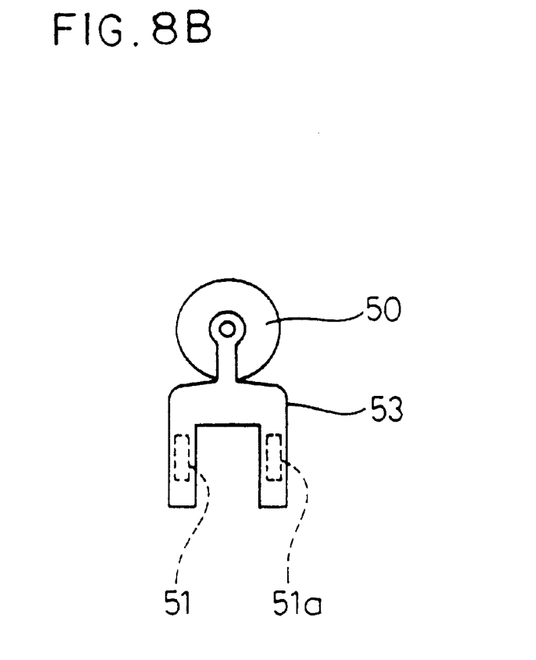

FIGS. 8A and 8B show a apparatus having a U-shaped coil support 53 mounted to the stand 50. In the front and back arm parts, two magnetic stimulation coils 51 and 51a wound in a vertical direction are embeded. If these coils are fed with current pulses having the same direction and timing, the magnetic fluxes are atracted to the countereparts due to a opposite polarity to each other, thereby the dispersing magnetic fluxes concentrate to the line connecting the centers of coils 51 and 51a, then reaching a deeper region with a effective level exceeding the threshold even though each one may not exceed the threshold.

Further, when coils 51 and 51a are mounted displaceably, the efficiently stimulated region can be varied during treatment.

Furthermore, three or more coils can be mounted.

As a further modification of this embodiment, in place of one of the two coils 51 and 51a, a highly permeable metal may be mounted. This arrangement allows a magnetic flux from the remaining coil to extend toward the metal so that magnetic flux converges along the line connecting the centers of the metal and the remaining coil 51 or 51a, allowing a deeper region to be stimulated with a lower voltage or a lower power consumption.

In addition, the metal, by shifting its position from the precisely confronting position to the coil 51 or 51a can change its most effective stimulating region. Further, when the metal is mounted in such a manner that its position can be varied, its position can be adjusted during treatment.

To the stationary coils illustrated in FIGS. 5 to 8, can be supplied with a cooling means to prevent the occurrence of low temperature burns. The cooling means may depend on the use of tap water or distillated water when treatment is made at home, or on the use of a freezer based on a freezing cycle, in place of the above-described cyclic cooling apparatus.

When a current pulse is passed through a coil with an air core, the resulting magnetic flux has the maximum density at the center thereof, and gradually decreases toward the periphery.

The higher the density of the magnetic flux, the larger the resulting eddy current proportional to the differential of the magnetic flux. Accordingly, in above embodiments including the one illustrated in FIG. 8, especially when the stimulation with pulses of a frequency of several Hz is made for the treatment of urge incontinence, iron or ferrite cores may be inserted at the air core portion, because the heat due to the resistive loss of current through the core will be negligible. Thereby, the flux converges toward the center, thus preventing from the spread to the periphery. This arrangement allows an efficient simulation by setting to the tip of the core toward, for example, an body portion having a low threshold out of the pudendal nerve.

In above embodiments, one large ring coil may be mounted instead of a plurality of coils.

Figure 9:
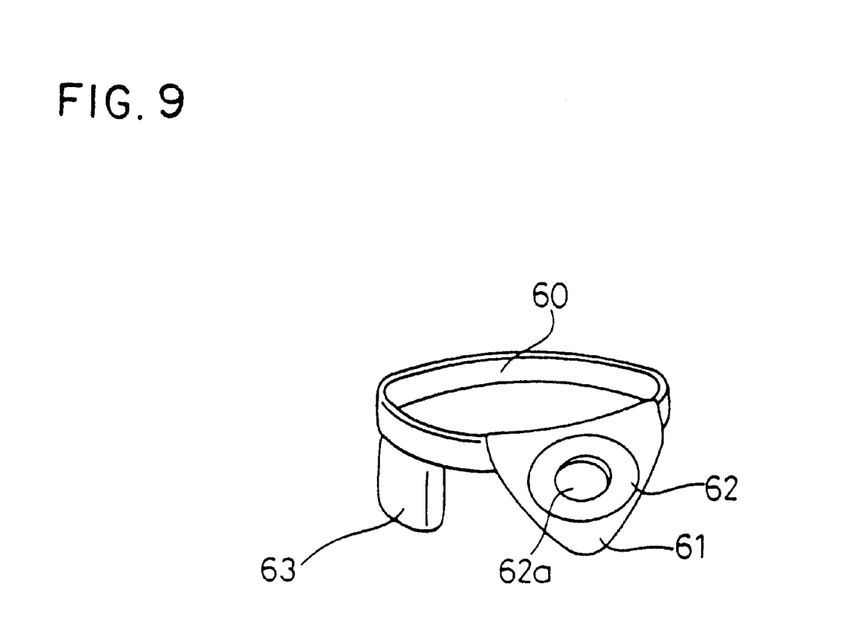
FIG. 9 is a perspective view of a portable type of the apparatus using a belt.

FIG. 9 illustrates a portable apparatus for treating urinary incontinence. This apparatus comprises a belt 60 which is to be wound around the waist of the patient as a body attached wear. A pocket 63 containing coil feed means for feeding a magnetic stimulation coil and a local cup 61 to which is mounted a case made of cloth or soft resin and containing the magnetic stimulation coil are hanged by the belt 60. The coil feed means is composed in a same manner with FIG. 3, using a battery as a DC source. The case is to be so positioned as to confront the pudendal region. This apparatus should be so constituted as to produce, provided that the battery voltage is about 20V, a magnetic flux of about 0.01–0.1 tesla when the maximum current of about 10 A is passed through the coil.

When the belt 60 is wound around the waist of the patient, for the treatment of urge incontinence, a magnetic flux develops toward the pudendal region, which results in selective stimulation of the pudendal nerve or its branches. Alternatively, when the frequency is switched to several tens Hz, a group of muscles forming the floor of pelvis and the external urethral sphincter contract under stimulation, which is effective for the treatment of stress incontinence. This apparatus can be worn or removed so easily that the patient rarely feels awkward even in the everyday activities. The patient, therefore, rarely shows an aversion toward its usage and continuation of the treatment.

Thus, usage of this apparatus brings about an obvious effect in a shorter period. However, during usage of this apparatus, the magnet stimulation coil develops heat of about 1–10 W. To dissolve that heat, as the case may be, it is possible to insert in the air core portion 62a of the coil a cooling element such as a peltier element which absorbs the heat when supplied from a battery. This will relieve the patient of discomfort due to heating. Alternatively, a cooling apparatus based on the use of a fan may be used instead of the above-described cooling element. This portable stimulating type can be constructed so as to produce a magnet flux as high as 1 tesla. The local cup 61 can be modified so as to take a form like a ring, or a band having surface fasteners at its ends so that it can be wound around the penis of the male patient.

Figure 10:
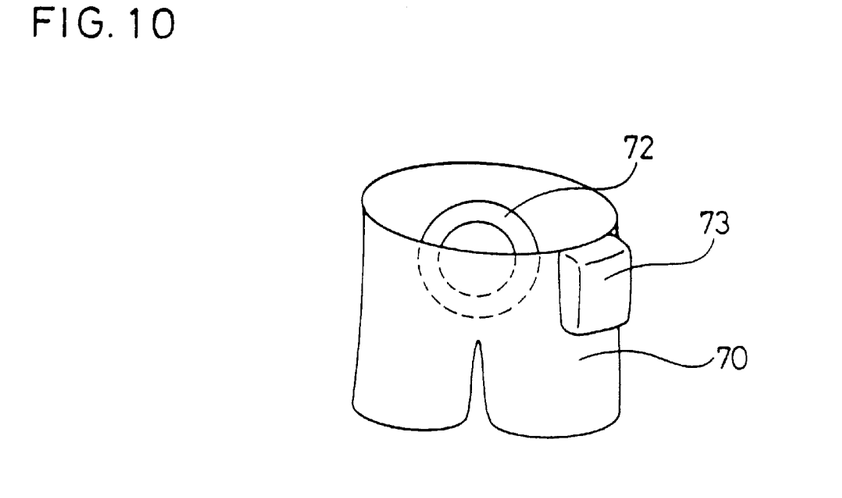
FIG. 10 is a perspective view of a portable type of the apparatus using undershorts.

FIG. 10 illustrates a portable apparatus for treating urinary incontinence comprising shorts as a body attached wear. A case 72 containing the magnetic stimulation coil is attached to the front part of the undershorts 70, and a pocket 73 containing coil feed means dependent on the use of a battery is fixed to the upper rim of the shorts 70. This apparatus, since the magnetic stimulation coil can be positioned to confront the lower abdomen, can be worn and removed with ease, and scarcely interferes with everyday activities.

Figure 11:
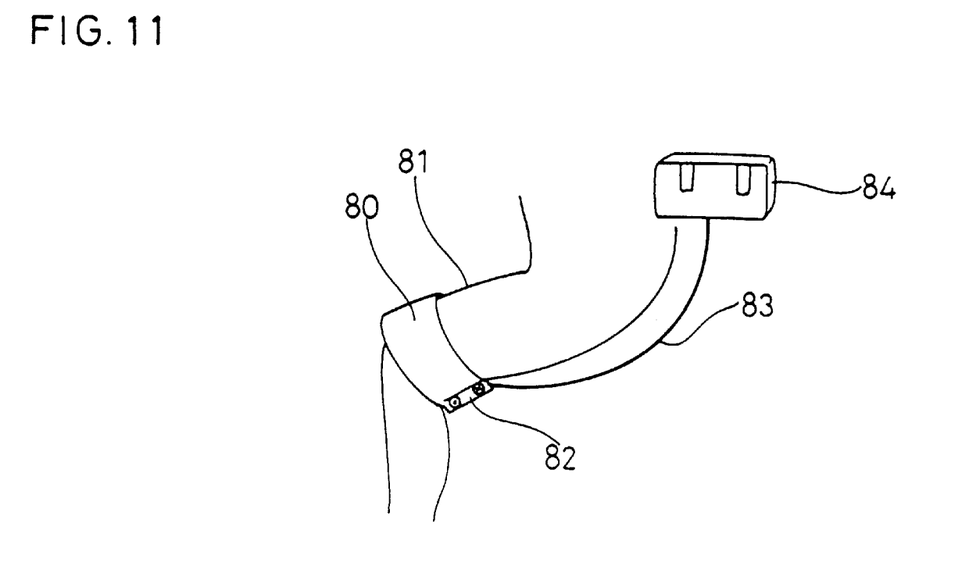
FIG. 11 is a perspective view of a portable type of the apparatus using an adhesive band.

FIG. 11 illustrates a portable apparatus for the treatment of urinary incontinence which is used for stimulation of the tibial nerve at the popliteal fossa. The reason why this type is devised is that the tibial nerve runs superficially at that part like the dorsal nerve of penis which distributes to the superficial structures of penis. The body attached wears consists of a adhesive band 80 attached to the lowest end of the femoral region 81 and suporting a case 82 containing a magnetic stimulation coil wound to the posterior part of knee, and a pocket 84 containing coil feed means from which is led out lead wires 83 connected to the magnetic stimulation coil and having a certain member to be engaged with the waist. The magnetic coil is composed of a winding of a litz wire with a diameter of about 0.5 mm, and is protected by a cover made of an elastic insulasive synthetic resin. This apparatus allows the magnetic coil to be flexibly bent so as to snugly fit onto the surface of the posterior part of the knee, and to stimulate with a minimum consumption of energy. This mode of stimulation has been confirmed effective for the treatment of urge incontinence. Adhesive gel conductors may be applied onto two portions of the knee facing to each other so as to easily flow the eddy current into the body. When the magnetic stimulation coil contained in the case 82 has an opening at its center, it is used as a mark to readily position the coil to a most effective body portion.

What is claimed is:

1. A method for treating incontinence comprising the steps of:

applying at least one magnetic stimulation coil to a body portion of a patient, providing at least one of a train and successive of current pulses to the magnetic stimulation coils, thereby producing magnetic flux pulses, and selecting a region to be stimulated by an eddy current induced by the magnetic flux pulses in a portion of the physiological body from the group consisting of branches from 2nd to 4th sacral nerves, the pelvic floor muscle group, pudendal nerve, external urethral muscle, tibial nerve, dorsal nerve of penis and, dorsal nerve of clitoris by developing magnetic flux from an anal region.

2. The method for treating incontinence according to claim 1, wherein the step of providing current pulses includes the step of providing at least one of the group consisting of a train of signal pulses, a train of double pulses and a train of bipolar pulses of current pulses to said at least one coil.

3. A method for treating incontinence comprising the steps of:

providing at least one magnetic stimulation coil, applying the at least one magnetic stimulation coil to a body portion of a patient in a range from the waist down to the feet, providing at least one of train and successive current pulses to the at least one magnetic stimulation coil, thereby producing magnetic flux pulses, having the patient carry the at least one magnetic stimulation coil, and providing coil feed means for providing current pulses to said at least one magnetic stimulation coil.

4. A method for treating incontinence comprising the steps of:

applying at least one magnetic stimulation coil to a body portion of a patient in a range from the waist down to the feet, providing at least one of train and successive current pulses to the magnetic stimulation coils, thereby producing magnetic flux pulses, and selecting a region to be stimulated by an eddy current induced by the magnetic flux pulses in a portion of the physiological body from the group consisting of branches from 2nd to 4th sacral nerves, the pelvic floor muscle group, pudendal nerve, external urethral muscle, tibial nerve, and dorsal nerve of the penis and dorsal nerve of the clitoris.

5. A method for treating incontinence comprising the step of:

providing at least two magnetic stimulation coils;

positioning a portion of the body to be stimulated between the at least two magnetic stimulation coils; and providing current pulses to the at least two coils, thereby producing magnetic flux pulses; and selecting the body portion to be stimulated by an eddy current induced by the magnetic flux pulses from the group consisting of branches from 2nd to 4th sacral nerves, the pelvic floor muscle group, pudendal nerve, external urethral muscle, tibial nerve, and dorsal nerve of penis and, dorsal nerve clitoris.

6. A method for treating incontinence comprising the steps of:

applying a plurality of magnetic stimulation coils to a body portion of a patient in a range from the waist down to the feet, and providing current pulses to magnetic stimulation coils, thereby producing magnetic flux pulses, independently feeding each of said plurality of magnetic stimulation coils so as to change the region where the eddy current is induced by the magnetic flux pulses.

7. The method for treating incontinence as described in claim 6 wherein at least two coils of said plurality of magnetic stimulation coils are connected in parallel to feed apparatus which includes a coil feed means to supply current to said at least two coils.

8. A magnetic stimulator comprising:

a coil tool provided with at least one magnetic stimulation coil which is adapted to be set to a body portion of a patient to be stimulated, said at least one coil including a hollow conduit passing therethrough having a first and second open end, said first and second ends each being connected to a pipe, said conduit and the pipe cooperating to permit refrigerant to pass through and cool the at least one coil during stimulation thereof.

9. The magnetic stimulator as described in claim 8 wherein said coil tool includes a seat which contains said at least one magnetic stimulation coil.

10. The magnetic stimulator as described in claim 8 wherein said coil tool consists of a bed which has said at least one magnetic stimulation coil installed at the region corresponding to a body portion in a range from the waist down to the feet.

11. The magnetic stimulator as described in claim 8 wherein said coil tool consists of a bed having a rail which guides a slider containing said at least one magnetic stimulation coil so as to slide said at least one coil at least between the waist and knees of the patient.

12. The magnetic stimulator as described in claim 8 wherein said coil tool consists of a stand positioned adjacent to a bed, and a coil supporting arm containing said at least one magnetic stimulation coil and being supported at a proximal end by the stand so as to swing between a position above the bed and a remote position.

13. The magnetic stimulator as described in claim 8 and further including at least two magnetic stimulation coils and wherein said coil tool consists of a stand, and a pair of semicircular coil supporting arms forming a ring adapted for embracing the patient, each of the pair of semicircular coil supporting arms containing one of said at least two magnetic stimulation coils, and the pair of supporting arms being hinged to the stand.

14. The magnetic stimulator as described in claim 8 wherein each pulse width of the magnetic flux pulses is 50 $\mu s$–5 ms.

15. The magnetic stimulator as described in claim 8, wherein said at least one coil is made of hollow conductor.

16. The magnetic stimulator as described in claim 8, wherein said pipe is an insulated pipe.

17. A magnetic stimulator comprising:

at least one magnetic stimulation coil for applying to a body portion of the patient, coil feed means for feeding said at least one magnetic stimulation coil so as to produce magnetic flux pulses therefrom, and a peltier element for absorbing heat generated during stimulation of said at least one coil operatively connected to said at least one coil.

18. A method for treating stress incontinence comprising the steps of:

applying at least one magnetic stimulation coil to a portion of a body of a patient selected from the group consisting of branches from 2nd to 4th sacral nerves, the pelvic floor muscle group, pudenal nerve, external urethral muscle, dorsal nerve of penis and, dorsal nerve of clitoris by developing magnetic flux from the anal region; and providing current pulses to said at least one magnetic stimulation coil, thereby producing magnetic flux pulses with frequency of several tens Hz.

19. The method for treating stress incontinence as described in claim 18, wherein said current pulses provided to said at least one magnetic stimulation coil are train of current pulses thereby producing a train of magnetic flux pulses.

20. The method for treating stress incontinence as described in claim 18, wherein said current pulses provided to said at least one magnetic stimulation coil are successive current pulses thereby producing successive magnetic flux pulses.

21. A method for treating urge incontinence comprising the steps of:

applying at least one magnetic stimulation coil to a portion of a body of a patient selected from the group consisting of branches from 2nd to 4th sacral nerves, the pelvic floor muscle group, pudendal nerve, external urethral muscle, dorsal nerve of penis and, dorsal nerve of clitoris; and providing current pulses to said at least one magnetic stimulation coil, thereby producing magnetic flux pulses with frequency of several Hz.

22. The method for treating urge incontinence as described in claim 21, wherein said step of applying at least one stimulation coil to a portion of a body of a patient is applied by developing magnetic flux from an anal region.

23. The method for treating urge incontinence as described in claim 21, wherein said current pulses provided to said magnetic stimulation coil are successive current pulses thereby producing successive magnetic flux pulses.

24. The method for treating incontinence as described in claim 21, wherein said current pulses provided to said magnetic stimulation coil are successive current pulses thereby producing successive magnetic flux pulses.

25. A method for treating incontinence comprising the steps of:

providing at least one magnetic stimulation coil;

providing a magnetic material having a high permeability;

applying the at least one magnetic stimulation coil and the magnetic material to a body portion of a patient in a range from the waist down to the feet; and providing current pulses to said at least one magnetic stimulation coil, thereby producing magnetic flux pulses.

26. The method for treating incontinence as described in claim 25, further comprising the step of placing said magnetic material on the abdomen of the patient to concentrate stray and diffusive magnetic fluxed to effective regions from the group consisting of the perineal nerve, the pudendal nerve, a group of pelvic floor muscles, and the external urethral sphincter.

27. A magnetic stimulator comprising:

at least one magnetic stimulation coil which is adapted to be set to a body portion of a patient;

a magnetic material having a high permeability, said at least one magnetic stimulation coil and magnetic material defining a space therebetween for receiving a portion of a patient's body for treatment; and a coil feed means for feeding said at least one magnetic stimulation coil so as to produce a series of magnetic flux pulses therefrom, the magnetic material concentrating stray and diffusive magnetic fluxed to effective regions of the patient's body.

28. A method for treating incontinence comprising the steps of:

provide at least one magnetic stimulation coil;

providing a magnetic material having a high permeability;

positioning the portion of the body between said at least one magnetic stimulation coil and said magnetic material;

providing current pulses to the magnetic stimulation coils, thereby producing magnetic flux pulses; and selecting a region to be stimulated by the eddy current induced by the magnetic flux pulses in a position of the physiological body from the group consisting of branches from 2nd to 4th sacral nerves, the pelvic floor muscle group, pudendal nerve, external urethral muscle, tibial nerve, dorsal nerve of penis and, dorsal nerve of clitoris.

* * * * *

UNITED STATES PATENT AND TRADEMARK OFFICE
CERTIFICATE OF CORRECTION

PATENT NO. : 5,984,854
DATED : November 16, 1999
INVENTOR(S) : Ishikawa et al.

It is certified that error appears in the above-identified patent and that said Letters Patent is hereby corrected as shown below:

IN THE SPECIFICATION:

In Column 6, Line 11, "apparatuss" should be --apparatus--;

In Column 7, Line 52, "add" should be --added--;

In Column 7, Line 51, "perihery" should be --periphery--;

In Column 4, Line 66, "hold coils" should be --mold coils--;

IN THE CLAIMS:

Claim 23, Lines 1-4, "The method for treating urge incontinence as described in claim 21, wherein said current pulses provided to said magnetic stimulation coil are successive current pulses thereby producing successive magnetic flux pulses" should be --The method for treating urge incontinence as described in claim 21, wherein said current pulses provided to said magnetic stimulation coil are train of current pulses thereby prodicing a train of magnetic flux pulses--; and

UNITED STATES PATENT AND TRADEMARK OFFICE
CERTIFICATE OF CORRECTION

PATENT NO.   : 5,984,854
DATED        : November 16, 1999
INVENTOR(S)  : Ishikawa et al It is certified that error appears in the above-identified patent and that said Letters Patent is hereby corrected as shown below:

<u>In Column 12, line 36</u>, "treating incontinence" should be --treating urge incontinence--.

Signed and Sealed this

Twelfth Day of December, 2000

Attest:

Q. TODD DICKINSON

*Attesting Officer*               *Director of Patents and Trademarks*